United States Patent
Atoguchi et al.

(10) Patent No.: US 6,441,250 B2
(45) Date of Patent: Aug. 27, 2002

(54) PROCESS FOR PRODUCING DIHYDRIC PHENOL

(75) Inventors: Takashi Atoguchi; Shigeru Yao; Tomonori Kanougi, all of Ichihara (JP)

(73) Assignee: UBE Industries, Ltd., Yamaguchi-ken (JP)

( * ) Notice: Subject to any disclaimer, the term of this patent is extended or adjusted under 35 U.S.C. 154(b) by 0 days.

(21) Appl. No.: 09/884,544

(22) Filed: Jun. 19, 2001

(30) Foreign Application Priority Data

Jun. 22, 2000 (JP) .......................................... 12-188095
May 7, 2001 (JP) .......................................... 13-136055

(51) Int. Cl.$^7$ ............................................. C07C 37/00
(52) U.S. Cl. ....................................................... 568/771
(58) Field of Search .......................................... 568/771

(56) References Cited

U.S. PATENT DOCUMENTS

| | | | |
|---|---|---|---|
| 3,580,956 A | | 5/1971 | Bloch |
| 4,078,006 A | | 3/1978 | Umemura et al. |
| 4,396,783 A | * | 8/1983 | Esposito |
| 4,578,521 A | | 3/1986 | Chang et al. |
| 5,331,103 A | * | 7/1994 | Costantini |
| 5,434,317 A | * | 7/1995 | Costantini |
| 6,262,315 B1 | * | 7/2001 | Inaba |

FOREIGN PATENT DOCUMENTS

FR  2693457  1/1994

OTHER PUBLICATIONS

English abstract of Japan Pat. No. 52065232 A, Date: May 30, 1977.
English abstract of Japan Pat. No. 52065233 A, Date: May 30, 1977.
English abstract of Japan Pat. No. 52078843 A, Date: Jul. 2, 1977.
English abstract of Japan Pat. No. 52142026 A, Date: Nov. 26, 1977.
English abstract of German Pat. No. 2514742 A, Date: Oct. 9, 1975.

* cited by examiner

*Primary Examiner*—Michael L. Shippen
(74) *Attorney, Agent, or Firm*—Jordan and Hamburg LLP

(57) ABSTRACT

There are disclosed a process for producing a dihydric phenol which comprises oxidizing a monohydric phenol by a peroxide compound in the presence of a β-zeolite, a ketone and a phosphoric acid, and a process for producing a dihydric phenol which comprises oxidizing a monohydric phenol in the presence of a β-zeolite, a ketone and a phosphoric acid, by feeding a monohydric phenol, hydrogen peroxide, a ketone and a phosphoric acid into a reactor in which a β-zeolite is charged, to oxidize the monohydric phenol into a dihydric phenol, and delivering the resultant reaction mixture from the reactor.

31 Claims, No Drawings

PROCESS FOR PRODUCING DIHYDRIC PHENOL

BACKGROUND OF THE INVENTION

1. Field of the Invention

This invention relates to a process for producing a dihydric phenol which comprises oxidizing a monohydric phenol by a peroxide compound in the presence of a ketone and a phosphoric acid.

2. Prior Art

As a process for producing a dihydric phenol by oxidizing a monohydric phenol by a peroxide compound in the presence of a catalyst, there has been known a process as mentioned below. For example, a process in which a reaction is conducted in the presence of a ketone and phosphoric acid using a catalyst such as sulfuric acid is disclosed in Japanese Provisional Patent Publications Nos. 65232/1977 and 65233/1977, etc. Sulfuric acid used in this process as a catalyst has a corrosive property, and therefore, a new catalyst substituting therefor has been desired to be developed. As a catalyst substituting sulfuric acid, for example, there have been descriptions on phosphotungstic acid and silicotungstic acid in Japanese Provisional Patent Publication No. 078843/1977, various kinds of sulfates in Japanese Provisional Patent Publication No. 130727/1975, and a clay mineral in Japanese Provisional Patent Publication No. 142026/1977, respectively. However, a yield of the product based on a peroxide compound is low, so that a development of a catalyst with a further higher activity has been expected.

SUMMARY OF THE INVENTION

An object of the present invention is to develop an acid catalyst with high activity and without a corrosive property in order to provide a process for producing a dihydric phenol with a high yield by oxidizing a monohydric phenol with a peroxide compound in the presence of a ketone and a phosphoric acid.

The present inventors have intensively studied to accomplish the above-mentioned object and as a result, they have found that a dihydric phenol can be obtained with a high yield by using a β-zeolite which has no corrosive property when a dihydric phenol is produced by oxidizing a monohydric phenol with a peroxide compound in the presence of a ketone and a phosphoric acid.

That is, the present invention is a process for producing a dihydric phenol which comprises oxidizing a monohydric phenol by a peroxide compound in the presence of a β-zeolite, a ketone and a phosphoric acid.

Also, the present invention is a process for producing a dihydric phenol which comprises oxidizing a monohydric phenol in the presence of a β-zeolite, a ketone and a phosphoric acid, by feeding a monohydric phenol, hydrogen peroxide, a ketone and a phosphoric acid into a reactor in which a β-zeolite is charged, to oxidize the monohydric phenol into a dihydric phenol and delivering the resultant reaction mixture from the reactor.

DESCRIPTION OF THE PREFERRED EMBODIMENT

In the following, the present invention will be explained in more detail.

As the monohydric phenol to be used in the present invention, there may be mentioned, for example, phenol, a monohydric monoalkyl phenol, a monohydric halogenated phenol and a monohydric polyalkyl phenol.

As the alkyl group contained in the monohydric monoalkyl phenol, there may be mentioned a straight or a branched alkyl group having 1 to 6 carbon atoms. A position of the alkyl group is not particularly limited as long as it does not participate in a reaction. As examples of these compounds, there may be mentioned o-, m- or p-cresol, o-, m- or p-ethylphenol, o-propylphenol, p-isopropylphenol, m-butylphenol, p-isobutylphenol, p-t-butylphenol, m-isobutylphenol, p-pentylphenol and p-hexylphenol.

As the halogen atom contained in the monohydric halogenated phenol, there may be mentioned a fluorine atom, a chlorine atom, a bromine atom and an iodine atom. A number and a position of the halogen atoms are not particularly limited as long as they do not participate in a reaction. As examples of these compounds, there may be mentioned o-, m- or p-fluorophenol, o-, m- or p-chlorophenol, o-, m- or p-bromophenol, o-, m- or p-iodophenol, 2,3-, 2,4-, 2,5-, 2,6-, 3,4- or 3,5-dichlorophenol, 2,3-, 2,4-, 2,5-, 2,6-, 3,4- or 3,5-dibromophenol, 2,3,4-, 2,3,5-, 2,3,6-, 2,4,5-, 2,4,6- or 3,4,5-trichlorophenol.

As the alkyl group contained in the monohydric polyalkyl phenol, there may be mentioned a straight or a branched alkyl group having 1 to 6 carbon atoms. A number and a position of the alkyl groups are not particularly limited as long as they do not participate in a reaction. As examples of these compounds, there may be mentioned 2,3-, 2,4-, 2,5-, 2,6-, 3,5- or 3,4-dimethylphenol, 2,3,4-trimethylphenol, 2,3,5-, 2,3,6- or 3,4,5-trimethylphenol, 2,4,5-trimethylphenol, 2,3,4,5- or 2,3,5,6-tetramethylphenol, 2-ethyl-3-methylphenol, 3-t-butyl-4-methylphenol, 2-isopropyl-5-methylphenol, 2-pentyl-6-methylphenol and 3-hexyl-5-methylphenol.

As examples of the ketone to be used in the present invention, there may be mentioned a monoketone and a diketone. As the monoketone, a noncyclic or cyclic monoketone is mentioned. As the noncyclic monoketone, there may be mentioned, for example, a straight or branched aliphatic monoketone having 3 to 20 carbon atoms, preferably 3 to 10 carbon atoms and an aromatic monoketone. Hydrogen atom of these compounds may be substituted by a halogen atom (a fluorine atom, a chlorine atom, a bromine atom or an iodine atom). A number and a position of the halogen atoms are not particularly limited as long as they do not participate in a reaction.

As the straight aliphatic monoketone, there may be mentioned, for example, acetone, methyl ethyl ketone, 2-pentanone, 3-pentanone, 2-hexanone, 2-heptanone, 3-heptanone, 4-heptanone, 2-octanone, 2-nonanone, 3-decanone, 6-undecanone, 2-tri-decanone, 7-tridecanone, 2-tetradecanone, 2-pentadecanone, 2-hexadecanone, 2-heptadecanone, 3-octadecanone, 4-nonadecanone, 1-chloro-2-propanone, 1-chloro-3-heptanone and 1-bromo-3-heptanone.

As the branched aliphatic monoketone, there may be mentioned, for example, 3-methyl-2-butanone, 3-methyl-2-pentanone, 4-methyl-2-pentanone, 3,3-dimethyl-2-butanone, 2,4-dimethyl-3-pentanone, 6-methyl-2-heptanone, 2,6-dimethyl-4-heptanone and 2,2,4,4-tetramethyl-3-heptanone. As the aromatic monoketone, there may be mentioned, for example, acetophenone, benzophenone, 1-phenyl-3-propanone, 1-phenyl-1-butanone, 1-phenyl-3-butanone, 1-phenyl-3-pentanone and 1,3-diphenyl-2-propanone.

As the cyclic monoketone, there may be mentioned, for example, a cycloalkyl monoketone having 5 to 12 carbon atoms. Hydrogen atoms of these compounds may be substituted by a halogen atom (a fluorine atom, a chlorine atom, a bromine atom and an iodine atom) or by a straight or a branched alkyl group having 1 to 6 carbon atoms. A number and a position of the substitute are not particularly limited as long as they do not participate in a reaction. As examples of these compounds, there may be mentioned cyclopentanone, cyclohexanone, cyclododecanone, 2-chlorocyclohexanone, 2-ethyl-1-cyclopentanone, 2-methyl-1-cyclohexanone.

As the diketone, there may be mentioned a noncyclic or cyclic diketone. As the noncyclic diketone, there may be mentioned, for example, a straight or a branched aliphatic diketone having 5 to 21 carbon atoms, preferably 5 to 12 carbon atoms and an aromatic diketone. Hydrogen atom of these compounds may be substituted by a halogen atom (a fluorine atom, a chlorine atom, a bromine atom or an iodine atom). A number and a position of the halogen atoms are not particularly limited as long as they do not participate in a reaction. As the straight aliphatic diketone, there maybe mentioned, for example, 2,3-butanedione, 2,4-pentanedione and 2,5-hexanedione. As the branched aliphatic diketone, there may be mentioned, for example, 2,5-dimethyl-3,4-hexanedione. As the aromatic diketone, there may be mentioned, for example, 1,2-diphenylethane-1,2-dione.

As the cyclic diketone, there may be mentioned, for example, a cyclic diketone having 5 to 12 carbon atoms. Hydrogen atom of these compounds may be substituted by a halogen atom (a fluorine atom, a chlorine atom, a bromine atom and an iodine atom) or by a straight or branched alkyl group having 1 to 6 carbon atoms. A number and a position of the substituent are not particularly limited as long as they do not participate in a reaction. As the cyclic diketone, there may be mentioned, for example, 1,4-cyclohexanedione.

Among the ketones to be used in the present invention, preferred are the straight or branched aliphatic monoketone or the cyclic monoketone, and more preferred are the straight or branched aliphatic monoketone, among which 4-methyl-2-pentanone and 3-pentanone are particularly preferred.

An amount of the ketone to be used is preferably 0.2:1 to 5:1 in terms of a molar ratio of the ketone to a peroxide compound (ketone:peroxide compound).

As the phosphoric acid to be used in the present invention, there may be mentioned, for example, orthophosphoric acid, pyrophosphoric acid, metaphosphoric acid, triphosphoric acid, tetraphosphoric acid, polyphosphoric acid, phosphoric anhydride and an aqueous phosphoric acid solution, among which the aqueous phosphoric acid solution is preferred. A concentration of the aqueous phosphoric acid solution is preferably 0.001 to 100% by weight.

An amount of the phosphoric acid to be used is preferably 0.0001:1 to 0.05:1 in terms of a weight ratio of the phosphoric acid to the monohydric phenol (phosphoric acid::monohydric phenol).

As the peroxide compound to be used in the present invention, there may be mentioned, inorganic peroxide compounds, for example, hydrogen peroxide, and organic peroxide compounds, for example, ketone peroxides and aliphatic percarboxylic acids.

As the ketone peroxides, there may be mentioned, for example, dialkyl ketone peroxides which have 3 to 20, preferably 3 to 10 carbon atoms, such as dimethyl ketone peroxide, diethyl ketone peroxide, methyl ethyl ketone peroxide, methyl-n-propyl ketone peroxide, methyl isopropyl ketone peroxide, and methyl isobutyl ketone peroxide.

As the aliphatic percarboxylic acids, there may be mentioned, for example, peracetic acid and perpropionic acid.

As hydrogen peroxide, 0.1% by weight or more of the aqueous hydrogen peroxide solution may be used, preferably 0.1 to 90% by weight, and more preferably 30 to 80% by weight.

Among the peroxide compounds to be used in the present invention, preferred are hydrogen peroxide and ketone peroxides. The ketone peroxides can be prepared by contacting ketone with hydrogen peroxide. The ketones to be used here are the same as mentioned before.

An amount of the peroxide compound to be used is preferably in the range of 1:1 to 1:100, more preferably in the range of 1:5 to 1:20 in terms of a molar ratio of the peroxide compound to the monohydric phenol.

In the present invention, a β-zeolite is used as a catalyst. As the β-zeolite, a proton type β-zeolite is preferred, among which a proton type β-zeolite carrying thereon at least one of an alkaline earth metal is especially preferred. A content of aluminum in the β-zeolite is preferably in the range of 1:10 to 1:10000 in terms of an atomic ratio of aluminum to silicon (Al:Si).

An amount of the β-zeolite to be used is preferably in the range of 1:1 to 1:500, more preferably in the range of 1:5 to 1:100 in terms of a weight ratio of the β-zeolite to the monohydric phenol (β-zeolite:monohydric phenol).

The β-zeolite ma y be prepared according to a method described in Journal of Physical Chemistry, 104 (2000), pp. 2853 to 2859, or a commercially available product may be preferably used.

The proton type β-zeolite is prepared according to a method described in the above-mentioned reference, etc. For example, it can be prepared by heating a β-zeolite in an aqueous solution containing an ammonium ion such as an aqueous solution of ammonium nitrate, ammonium chloride, etc. (an ammonium salt concentration: 0.1 to 40% by weight) at 20 to 120° C., for 1 to 20 hours, washing the resulting material by deionized water, etc., drying the same at 20 to 150° C., and calcining the same at about 300 to 650° C. for 1 to 10 hours.

The proton type β-zeolite carrying thereon an alkaline earth metal may be obtained by introducing alkaline earth metals to the above-mentioned proton type β-zeolite. As the alkaline earth metal, there may be mentioned beryllium, magnesium, calcium, strontium, and barium, among which magnesium, calcium, strontium and barium are preferable. As a method for introducing the metals, methods such as a conventionally used ion-exchange method, impregnation method, chemical vapor deposition (CVD) method, mechanical kneading method and the like are applicable, among which the ion-exchange method is preferable.

The proton type β-zeolite carrying thereon an alkaline earth metal can be prepared by the ion-exchange method according to a method described in Monthly Journal of Institute of Industrial Science, 21, 7 (1969), pp. 453 to 454. For example, it can be prepared by heating a β-zeolite in an aqueous solution containing alkaline earth metal ions such as an aqueous solution of a nitrate, a hydrochloride and a sulfate of an alkaline earth metal (a concentration of the alkaline earth metal salt: 0.1 to 40% by weight) at 20 to 120° C., for 1 to 20 hours, washing the resulting material with deionized water, etc., drying the same at 20 to 150° C. for 5 minutes to 24 hours, and calcining the same at about 300 to 650° C. for 1 to 10 hours. An amount of the alkaline earth metal ion introduced into the proton type β-zeolite is preferably in the range of 0.0001 to 10, more preferably 0.01 to 1, in terms of an atomic ratio of $M^{2+}/Al$ ($M^{2+}$ represents an alkaline earth metal ion).

A shape of the β-zeolite to be used may be mentioned powder, a granule, a pellet and the like.

As a shape of the β-zeolite suitable for the preparation method of the dihydric phenol, for example, when a liquid phase batch system reactor is used for preparation, powder is preferably used, and when a liquid phase flow system reactor is used for preparation, a pellet and the like is preferably used.

In the preparation of the dihydric phenol, the reaction temperature is preferably 20 to 250° C., more preferably 40 to 150° C. The reaction time is not limited although it depends on a kind of the catalyst used and the reaction temperature employed. In addition, although the reaction can be conducted under an atmospheric pressure, it may be conducted under a reduced or increased pressure. The reaction can be conducted in a liquid phase, by a batch system, a flow system, a trickle bed system, etc.

In the process of the present invention, optionally, a complexing agent for metal ions, for example, monoalkyl phosphates and dialkyl phosphates, may be employed.

In the process of the present invention, the reaction is carried out, for example, by feeding a monohydric phenol, hydrogen peroxide, a ketone and a phosphoric acid into a reactor in which a β-zeolite is charged, to oxidize the monohydric phenol into a dihydric phenol, and delivering the resultant reaction mixture from the reactor.

The dihydric phenol to be produced in the present invention is obtained as one kind or a mixture of several kinds corresponding to the structure of a monohydric phenol used as a starting material. In addition, these dihydric phenols can be obtained by separation and purification according to the conventional method.

EXAMPLES

In the following, the present invention will be explained in more detail by referring to Examples and Comparative examples.

Incidentally, the scope of the present invention is not limited by these Examples.

Reagents used in these Examples are of Special Grade by Wako Pure Chemical Industries.

A yield of the dihydric phenol was obtained in accordance with the following equation. Incidentally, analysis was conducted by a gas chromatography.

$$\text{(Total yield of dihydric phenol)} = \frac{\text{(A molar number of formed dihydric phenol)}}{\text{(A molar number of charged peroxide compound)}} \times 100 \, (\%)$$

Reference Example 1

Preparation of a Proton Type β-zeolite Carrying Strontium Ion 20 ml of an aqueous solution containing strontium ion was prepared by dissolving 0.47 g of strontium nitrate in 20 ml of ultrapure water. To the obtained solution was immersed 2 g of a proton type β-zeolite manufactured by Zeolyst International and ion-exchange was conducted between proton and strontium ion while keeping the temperature at 85° C. for 14 hours. The obtained suspension was filtered by suction, dried at 110° C., and calcined at 550° C. for 2.5 hours to obtain 1.9 g of a proton type β-zeolite carrying strontium ions thereon. According to ICP (Inductively Coupled Plasma) emission spectrometry, it was shown that a ratio (atomic ratio) of the strontium ions introduced into the β-zeolite relative to Al ($Sr^{2+}/Al$) was 0.31.

Reference Example 2

Preparation of a Proton Type β-zeolite Carrying Barium Ion 20 ml of an aqueous solution containing barium ion was prepared by dissolving 0.58 g of barium nitrate in 20 ml of ultrapure water. To the obtained solution was immersed 2 g of the proton type β-zeolite manufactured by Zeolyst International and ion-exchange was conducted between proton and barium ion while keeping the temperature at 85° C. for 14 hours. The obtained suspension was filtered by suction, dried at 110° C., and calcined at 550° C. for 2.5 hours to obtain 1.9 g of a proton type β-zeolite carrying barium ions thereon. According to ICP emission spectrometry, it was shown that a ratio (atomic ratio) of the barium ions introduced into the β-zeolite relative to Al ($Ba^{2+}/Al$) was 0.34.

Reference Example 3

Preparation of a Proton Type β-zeolite Carrying Magnesium Ion

Preparation was conducted in the same way as in Reference Example 2, except that 0.57 g of magnesium nitrate hexahydrate was used.

As a result, 1.9 g of a proton type β-zeolite carrying magnesium ions thereon was obtained. According to ICP emission spectrometry, it was shown that a ratio (atomic ratio) of magnesium ions introduced into the β-zeolite relative to Al ($Mg^{2+}/Al$) was 0.29.

Reference Example 4

Preparation of a Proton Type β-zeolite Carrying Calcium Ion

Preparation was conducted in the same way as in Reference Example 2, except that 0.52 g of calcium nitrate tetrahydrate was used.

As a result, 1.9 g of a proton type β-zeolite carrying calcium ions thereon was obtained. According to ICP emission spectrometry, it was shown that a ratio (atomic ratio) of calcium ions introduced into the β-zeolite relative to Al ($Ca^{2+}/Al$) was 0.28.

Example 1

In 300 ml of a flask were charged 0.20 g of a proton type β-zeolite manufactured by Zeolyst International, 10.00 g of phenol, 0.60 g of 4-methyl-2-pentanone and 0.03 g of a 85% by weight aqueous phosphoric acid solution, and after replacing the inner atmosphere with a nitrogen atmosphere, a temperature of the mixture was raised up to 80° C. under stirring. At the same temperature, 0.62 g of a 30% by weight aqueous hydrogen peroxide solution was added dropwise to the mixture. Subsequently, the temperature was maintained for 30 minutes to conduct the reaction.

As a result, a yield of the dihydric phenol was 58% for catechol and 40% for hydroquinone. A total yield of hydroquinone and catechol was 98%. The reaction mixture was slightly colored to pale yellow and substantially no accumulation of tar component was observed.

Example 2

A reaction was carried out in the same manner as in Example 1 except for changing the reaction temperature to 60° C.

A yield of the dihydric phenol was 55% for catechol and 38% for hydroquinone. A total yield of hydroquinone and catechol was 93%. The reaction mixture was slightly colored to pale yellow and substantially no accumulation of tar component was observed.

Comparative Example 1

In 300 ml of a flask were charged 0.04 g of 95% by weight sulfuric acid, 10.00 g of phenol, 0.60 g of 4-methyl-2-pentanone and 0.03 g of a 85% by weight aqueous phosphoric acid solution, and after replacing the inner atmosphere with a nitrogen atmosphere, a temperature of the mixture was raised up to 80° C. under stirring. At the same temperature, 0.63 g of a 30% by weight aqueous hydrogen peroxide solution was added dropwise to the mixture. Subsequently, the temperature was maintained for 30 minutes to conduct the reaction.

As a result, a yield of the dihydric phenol was 50% for catechol and 33% for hydroquinone. A total yield of hydroquinone and catechol was 83%. The reaction mixture was strongly colored to dark brown and accumulation of tar components was observed.

Comparative Example 2

A reaction was carried out in the same manner as in Comparative example 1 except for changing the reaction temperature to 60° C.

As a result, a yield of the dihydric phenol was 52% for catechol and 34% for hydroquinone. A total yield of hydroquinone and catechol was 86%. The reaction mixture was strongly colored to dark brown and accumulation of tar components was observed.

Comparative Example 3

A reaction was carried out in the same manner as in Example 1 except for replacing the catalyst with 0.20 g of a proton-type ZSM-5 zeolite manufactured by Nikki Universal Co.

As a result, a yield of the dihydric phenol was 15% for catechol and 8% for hydroquinone. A total yield of hydroquinone and catechol was 23%. The reaction mixture was strongly colored to dark brown and accumulation of tar components was observed.

Example 3

In 300 ml of a flask were charged 0.20 g of a proton type β-zeolite manufactured by Zeolyst International, 10.00 g of phenol, 0.27 g of 3-pentanone and 0.02 g of 85% by weight aqueous phosphoric acid solution, and after replacing the inner atmosphere with a nitrogen atmosphere, a temperature of the mixture was raised up to 80° C. under stirring. At the same temperature, 0.10 g of a 60% by weight aqueous hydrogen peroxide solution was added dropwise to the mixture, and 1.5 minutes later, additional 0.10 g, and 3 minutes later, further additional 0.10 g of the same was added dropwise to proceed the reaction for 5 minutes from the first dropwise addition.

As a result, a yield of the dihydric phenol was 50% for catechol and 35% for hydroquinone. A total yield of hydroquinone and catechol was 85%. The reaction mixture was slightly colored to pale yellow and substantially no accumulation of tar component was observed.

Example 4

A reaction was carried out in the same manner as in Example 3 except for changing the reaction temperature to 100° C.

A yield of the dihydric phenol was 51% for catechol and 34% for hydroquinone. A total yield of hydroquinone and catechol was 85%. The reaction mixture was slightly colored to pale yellow and substantially no accumulation of tar component was observed.

Example 5

A reaction was carried out in the same manner as in Example 3 except for replacing the catalyst with 0.20 g of the proton type β-zeolite carrying strontium ions of Reference Example 1.

As a result, a yield of the dihydric phenol was 51% for catechol and 38% for hydroquinone. A total yield of hydroquinone and catechol was 89%. The reaction mixture was slightly colored to pale yellow and substantially no accumulation of tar component was observed.

Example 6

A reaction was carried out in the same manner as in Example 5 except for changing the reaction temperature to 100° C.

As a result, a yield of the dihydric phenol was 53% for catechol and 39% for hydroquinone. A total yield of hydroquinone and catechol was 92%. The reaction mixture was slightly colored to pale reddish brown and substantially no accumulation of tar component was observed.

Example 7

A reaction was carried out in the same manner as in Example 3 except for replacing the catalyst with 0.20 g of the proton type β-zeolite carrying barium ions of Reference Example 2.

As a result, a yield of the dihydric phenol was 49% for catechol and 37% for hydroquinone. A total yield of hydroquinone and catechol was 86%. The reaction mixture was slightly colored to pale yellow and substantially no accumulation of tar component was observed.

Example 8

A reaction was carried out in the same manner as in Example 7 except for changing the reaction temperature to 100° C.

As a result, a yield of the dihydric phenol was 55% for catechol and 39% for hydroquinone. A total yield of hydroquinone and catechol was 94%. The reaction mixture was slightly colored to pale reddish brown and substantially no accumulation of tar component was observed.

Example 9

A reaction was carried out in the same manner as in Example 5 except for replacing the catalyst with 0.20 g of the proton type β-zeolite carrying magnesium ions of Reference Example 3 and changing the reaction temperature to 100° C.

As a result, a yield of the dihydric phenol was 54% for catechol and 39% for hydroquinone. A total yield of hydroquinone and catechol was 93%. The reaction mixture was slightly colored to pale reddish brown and substantially no accumulation of tar component was observed.

Example 10

A reaction was carried out in the same manner as in Example 5 except for replacing the catalyst with 0.20 g of the proton type β-zeolite carrying calcium ions of Reference Example 4.

As a result, a yield of the dihydric phenol was 48% for catechol and 36% for hydroquinone. A total yield of hydroquinone and catechol was 84%. The reaction mixture was slightly colored to pale yellow and substantially no accumulation of tar component was observed.

Example 11

A reaction was carried out in the same manner as in Example 10 except for changing the reaction temperature to 100° C.

As a result, a yield of the dihydric phenol was 56% for catechol and 40% for hydroquinone. A total yield of hydroquinone and catechol was 96%. The reaction mixture was slightly colored to pale reddish brown and substantially no accumulation of tar component was observed.

Comparative Example 4

A reaction was carried out in the same manner as in Example 4 except for replacing the catalyst with 0.04 g of 95% by weight sulfuric acid.

As a result, a yield of the dihydric phenol was 44% for catechol and 29% for hydroquinone. A total yield of hydroquinone and catechol was 73%. The reaction mixture was strongly colored to dark brown and accumulation of tar components was observed.

Comparative Example 5

A reaction was carried out in the same manner as in Example 4 except for replacing the catalyst with 0.20 g of a proton type Y-zeolite manufactured by Nikki Universal Co. (Si:Al=10:1).

As a result, a yield of the dihydric phenol was 3% for catechol and 1% for hydroquinone. A total yield of hydroquinone and catechol was 4%. The reaction mixture was strongly colored to dark brown and accumulation of tar components was observed.

Comparative Example 6

A reaction was carried out in the same manner as in Example 4 except for replacing the catalyst with 0.20 g of a proton type Y-zeolite (Si:Al=24:1).

As a result, a yield of the dihydric phenol was 11% for catechol and 5% for hydroquinone. A total yield of hydroquinone and catechol was 16%. The reaction mixture was strongly colored to dark brown and accumulation of tar components was observed.

The results of Examples 1 to 12 and Comparative Examples 1 to 6 are shown in Table 1.

TABLE 1

| | Catalyst | | $H_2O_2$ Concentration (%) | Reaction Temperature (° C.) | Reaction Time (min) | CL Yield (%) | HQ Yield (%) | CL + HQ Yield (%) |
|---|---|---|---|---|---|---|---|---|
| | Kind | Amount (g) | | | | | | |
| Example 1 | H/β | 0.2 | 30 | 80 | 30 | 58 | 40 | 98 |
| Example 2 | H/β | 0.2 | 30 | 60 | 30 | 55 | 38 | 93 |
| Comparative Example 1 | $H_2SO_4$ | 0.04 | 30 | 80 | 30 | 50 | 33 | 83 |
| Comparative Example 2 | $H_2SO_4$ | 0.04 | 30 | 60 | 30 | 52 | 34 | 86 |
| Comparative Example 3 | H/ZSM-5 | 0.2 | 30 | 80 | 30 | 8 | 15 | 23 |
| Example 3 | H/β | 0.2 | 60 | 60 | 5 | 50 | 35 | 85 |
| Example 4 | H/β | 0.2 | 60 | 100 | 5 | 51 | 34 | 85 |
| Example 5 | Sr,H/β | 0.2 | 60 | 60 | 5 | 51 | 38 | 89 |
| Example 6 | Sr,H/β | 0.2 | 60 | 100 | 5 | 53 | 39 | 92 |
| Example 7 | Ba,H/β | 0.2 | 60 | 60 | 5 | 49 | 37 | 86 |
| Example 8 | Ba,H/β | 0.2 | 60 | 100 | 5 | 55 | 39 | 94 |
| Example 9 | Mg,H/β | 0.2 | 60 | 100 | 5 | 54 | 39 | 93 |
| Example 10 | Ca,H/β | 0.2 | 60 | 60 | 5 | 48 | 36 | 84 |
| Example 11 | Ca,H/β | 0.2 | 60 | 100 | 5 | 56 | 40 | 96 |
| Comparative Example 4 | $H_2SO_4$ | 0.04 | 60 | 60 | 5 | 44 | 29 | 73 |
| Comparative Example 5 | H/Y | 0.2 | 60 | 100 | 5 | 3 | 1 | 4 |
| Comparative Example 6 | H/Y | 0.2 | 60 | 100 | 5 | 11 | 5 | 16 |

CL: catechol, HQ: hydroquinone
H/β: proton type β-zeolite
H/ZSM-5: proton type ZSM-5-zeplite
Sr, H/β: proton type β-zeolite carrying strontium ion
Ba, H/β: proton type β-zeolite carrying barium ion
Mg, H/β: proton type β-zeolite carrying magnesium ion
Ca, H/β: proton type β-zeolite carrying calcium ion
H/Y: proton type Y-zeolite (Comparative Example 5; Si:Al: = 10:1, Comparative Example 6; Si:Al = 24:1)

According to the process of the present invention wherein a β-zeolite without a corrosive property is used as a catalyst, a dihydric phenol can be obtained with a high yield when a monohydric phenol is oxidized by a peroxide compound in the presence of a ketone and a phosphoric acid, without causing accumulation or coking of tar components.

What is claimed is:

1. A process for producing a dihydric phenol which comprises oxidizing a monohydric phenol by a peroxide compound in the presence of a β-zeolite, a ketone and a phosphoric acid.

2. The process for producing a dihydric phenol according to claim 1, wherein the β-zeolite is a proton type β-zeolite.

3. The process for producing a dihydric phenol according to claim 2, wherein the proton type β-zeolite is a proton type β-zeolite carrying thereon an alkaline earth metal.

4. The process for producing a dihydric phenol according to claim 1, wherein the β-zeolite contains aluminum in a ratio of 1:10 to 1:10000 in terms of an atomic ratio of aluminum to silicon.

5. The process for producing a dihydric phenol according to claim 1, wherein the β-zeolite is used in an amount of 1:1 to 1:500 in terms of a weight ratio of the β-zeolite based on the monohydric phenol.

6. The process for producing a dihydric phenol according to claim 1, wherein the β-zeolite is used in an amount of 1:5 to 1:100 in terms of a weight ratio of the β-zeolite based on the monohydric phenol.

7. The process for producing a dihydric phenol according to claim 3, wherein the alkaline earth metal is at least one selected from the group consisting of beryllium, magnesium, calcium, strontium and barium.

8. The process for producing a dihydric phenol according to claim 3, wherein the alkaline earth metal is at least one selected from the group consisting of magnesium, calcium, strontium and barium.

9. The process for producing a dihydric phenol according to claim 3, wherein the proton type β-zeolite carrying thereon an alkaline earth metal is prepared by an ion-exchange method.

10. The process for producing a dihydric phenol according to claim 3, wherein the proton type β-zeolite carrying thereon an alkaline earth metal is prepared by introducing the alkaline earth metal into the proton type β-zeolite in a ratio of 0.0001 to 10 in terms of an atomic ratio of $M^{2+}/Al$ where $M^{2+}$ represents an alkaline earth metal ion.

11. The process for producing a dihydric phenol according to claim 3, wherein the proton type β-zeolite carrying thereon an alkaline earth metal is prepared by introducing the alkaline earth metal to the proton type β-zeolite in a ratio of 0.01 to 1 in terms of an atomic ratio of $M^{2+}/Al$ where $M^{2+}$ represents an alkaline earth metal ion.

12. The process for producing a dihydric phenol according to claim 1, wherein the monohydric phenol is selected from the group consisting of phenol, a monohydric monoalkylphenol, a monohydric halogenated phenol and a monohydric polyalkyl-phenol.

13. The process for producing a dihydric phenol according to claim 1, wherein the ketone is a monoketone or a diketone.

14. The process for producing a dihydric phenol according to claim 1, wherein the ketone is selected from the group consisting of a straight aliphatic monoketone, a branched aliphatic monoketone and a cyclic monoketone.

15. The process for producing a dihydric phenol according to claim 1, wherein the ketone is a straight aliphatic monoketone or a branched aliphatic monoketone.

16. The process for producing a dihydric phenol according to claim 1, wherein the ketone is 4-methyl-2-pentanon or 3-pentanone.

17. The process for producing a dihydric phenol according to claim 1, wherein the phosphoric acid is selected from the group consisting of orthophosphoric acid, pyrophosphoric acid, metaphosphoric acid, triphosphoric acid, tetraphosphoric acid, polyphosphoric acid, phosphoric anhydride and an aqueous phosphoric acid solution.

18. The process for producing a dihydric phenol according to claim 1, wherein the phosphoric acid is an aqueous phosphoric acid solution.

19. The process for producing a dihydric phenol according to claim 1, wherein the phosphoric acid is used in an amount of 0.0001:1 to 0.05:1 in terms of a weight ratio of the phosphoric acid relative to the monohydric phenol.

20. The process for producing a dihydric phenol according to claim 1, wherein the peroxide compound is hydrogen peroxide, ketone peroxides or aliphatic percarboxylic acids.

21. The process for producing a dihydric phenol according to claim 1, wherein the peroxide compound is hydrogen peroxide or ketone peroxides.

22. The process for producing a dihydric phenol according to claim 21, wherein the ketone peroxide is at least one selected from dialkylketone peroxides which have 3 to 20 carbon atoms.

23. The process for producing a dihydric phenol according to claim 1, wherein the peroxide compound is used in an amount of 1:1 to 1:100 in terms of a molar ratio of hydrogen peroxide to the monohydric phenol.

24. The process for producing a dihydric phenol according to claim 1, wherein the peroxide compound is used in an amount of 1:5 to 1:20 in terms of a molar ratio of hydrogen peroxide to the monohydric phenol.

25. The process for producing a dihydric phenol according to claim 1, wherein the reaction is carried out at a temperature of 20 to 250° C.

26. The process for producing a dihydric phenol according to claim 1, wherein the reaction is carried out at a temperature of 40 to 150° C.

27. A process for producing a dihydric phenol which comprises oxidizing a monohydric phenol in the presence of a β-zeolite, a ketone and a phosphoric acid, by feeding a monohydric phenol, hydrogen peroxide, a ketone and a phosphoric acid into a reactor in which a β-zeolite is charged, to oxidize the monohydric phenol into a dihydric phenol, and delivering the resultant reaction mixture from the reactor.

28. The process for producing a dihydric phenol according to claim 27, wherein the β-zeolite is a proton type β-zeolite.

29. The process for producing a dihydric phenol according to claim 28, wherein the proton type β-zeolite is a proton type β-zeolite carrying thereon an alkaline earth metal.

30. The process for producing a dihydric phenol according to claim 29, wherein the alkaline earth metal is at least one selected from the group consisting of beryllium, magnesium, calcium, strontium and barium.

31. The process for producing a dihydric phenol according to claim 27, wherein the β-zeolite has a shape of powder, a granule or a pellet.

* * * * *